US010327681B2

(12) United States Patent
Doyle, III et al.

(10) Patent No.: US 10,327,681 B2
(45) Date of Patent: Jun. 25, 2019

(54) GLUCOSE RATE INCREASE DETECTOR: A MEAL DETECTION MODULE FOR THE HEALTH MONITORING SYSTEM

(71) Applicant: The Regents of the University of California, Oakland, CA (US)

(72) Inventors: Francis J. Doyle, III, Cambridge, MA (US); Rebecca Harvey, Santa Barbara, CA (US); Eyal Dassau, Cambridge, MA (US); Howard Zisser, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 218 days.

(21) Appl. No.: 15/149,129

(22) Filed: May 7, 2016

(65) Prior Publication Data
US 2016/0256087 A1    Sep. 8, 2016

Related U.S. Application Data

(63) Continuation of application No. PCT/US2014/062991, filed on Oct. 29, 2014.

(60) Provisional application No. 61/903,965, filed on Nov. 14, 2013.

(51) Int. Cl.
| | |
|---|---|
| *A61B 5/145* | (2006.01) |
| *G16H 40/63* | (2018.01) |
| *A61B 5/00* | (2006.01) |
| *A61M 5/172* | (2006.01) |
| *G06F 19/00* | (2018.01) |

(52) U.S. Cl.
CPC .......... *A61B 5/14532* (2013.01); *A61B 5/725* (2013.01); *A61B 5/7235* (2013.01); *A61B 5/7275* (2013.01); *A61B 5/746* (2013.01); *A61M 5/1723* (2013.01); *G06F 19/3456* (2013.01); *G06F 19/3475* (2013.01); *G16H 40/63* (2018.01); *A61M 2230/201* (2013.01)

(58) Field of Classification Search
CPC ... A61B 5/14532; A61B 5/7235; A61B 5/725; A61B 5/7275; A61B 5/746; A61M 5/1723; A61M 2230/201; G06F 19/3406; G06F 19/3456; G06F 19/3475
USPC ......................................... 600/309, 345–366
See application file for complete search history.

(56) References Cited

U.S. PATENT DOCUMENTS

| | | | | |
|---|---|---|---|---|
| 9,171,343 | B1* | 10/2015 | Fischell | ................. G06Q 50/22 |
| 2011/0028817 | A1* | 2/2011 | Jin | ....................... A61B 5/0002 |
| | | | | 600/365 |
| 2012/0123234 | A1* | 5/2012 | Atlas | .................... A61B 5/7264 |
| | | | | 600/365 |
| 2015/0018633 | A1* | 1/2015 | Kovachev | ............ A61B 5/0022 |
| | | | | 600/301 |

FOREIGN PATENT DOCUMENTS

| | | | | |
|---|---|---|---|---|
| WO | WO 2012178134 | A2 * | 12/2012 | ........... A61B 5/0022 |
| WO | WO 2015073211 | A1 * | 5/2015 | ........... A61B 5/7235 |

\* cited by examiner

*Primary Examiner* — Navin Natnithithadha
(74) *Attorney, Agent, or Firm* — Richard Aron Osman

(57) ABSTRACT

A glucose rate increase detector (GRID) for use in an artificial pancreas (AP), wherein the GRID detects in a person persistent increases in glucose associated with a meal, and either triggers a meal bolus to blunt meal peak safely, during closed-loop control, or alerts the person to bolus for a meal, during open-loop control.

20 Claims, 6 Drawing Sheets

GLUCOSE RATE INCREASE DETECTOR: A MEAL DETECTION MODULE FOR THE HEALTH MONITORING SYSTEM

This invention was made with government support under Grant Numbers DP3DK094331 and ROIDK085628 awarded by the National Institutes of Health (NIH). The government has certain rights in the invention.

INTRODUCTION

The primary goal of the artificial pancreas (AP) is to eliminate the occurrence of severe hypoglycemia and reduce the time spent in hyperglycemia (>180 mg/dL) in an effort to improve quality of life and reduce long-term complications.[1] Safe and effective control of type 1 diabetes mellitus (T1DM) using an AP has been researched widely for several decades, with many advances, but several challenges remain, including overcoming large meal disturbances, the effects of exercise, and the delays associated with subcutaneous glucose sensing and insulin delivery.[2] One of the most challenging aspects of the diabetes therapy routine is dealing with meals, and it has been shown that inaccurate estimation of meal sizes occurs frequently, resulting in additional glucose fluctuations.[3] Recent behavioral studies have also shown that people with T1DM are interested in an automated system but are concerned with relinquishing full control.[4,5] Therefore, an automatic AP that is safe and robust to daily living conditions and is trusted by the users is critical.

The AP is a multi-layer device that will contain several features, including a core glucose controller, devices for monitoring of glucose and possibly other biologically relevant compounds or signals, software to interface with the user, safety systems to monitor the status of the system, and telemedicine to convey information about the system to the user and family and/or medical personnel. The core of the AP is the controller, the design of which has been explored by several research teams, with promising results[6-11]. Continuous glucose monitoring (CGM) devices and insulin pumps are continually being improved, and are at a performance level that enables automatic control.[12, 13] Currently, longer clinical trials with several meals and exercise are being performed with good results.[6, 14] Generally, the trials with meals larger than 50 g of carbohydrate (CHO) use a feed-forward approach, announcing meals and giving a full or partial bolus near meal time.[10, 15-17] This approach is taken due to the large glucose excursion caused by high CHO meals and the delays in subcutaneous glucose sensing and insulin action. For fully automatic control to be possible with the currently available glucose sensing and insulin delivery routes, meal detection must be integrated into the control scheme.

Several types of meal detection algorithms have been devised and studied in recent years.[18-21] In those cases, 1 minute sampling was used, which may increase the speed of detection and allow for increased accuracy. At this time, however, most CGMs provide data at a 5 minute sampling time. In Dassau et al.[18], the algorithms were tuned using data with withheld boluses, enhancing the meal excursion and allowing for higher sensitivity and faster detection. In addition, only isolated meals were evaluated, not full traces with several meals, and other disturbances. Some of the algorithms were trained and tested on 1 minute simulation data, with very little noise and disturbances.[19, 20] This disclosure provide, inter alia, an algorithm that has been trained and tested on clinical data that was in fully closed-loop mode, a reasonable model for the actual conditions in which meal detection will be utilized.

The Glucose Rate Increase Detector (GRID) is a module of the Health Monitoring System (HMS) that has been designed as a component of the AP that operates in parallel to the controller. The objective of the GRID is to detect persistent increases in glucose associated with a meal, and trigger a meal bolus to blunt the meal peak safely. It may be used in open-loop control, closed-loop control with user input, or fully automatic closed-loop control.

SUMMARY OF THE INVENTION

Glucose management using continuous glucose monitoring and insulin pumps as well as the use of an artificial pancreas (AP) system that implements intensive insulin therapy has an inherent risk of adverse events such as hypoglycemia and hyperglycemia. Real-time prediction of pending adverse events by the Health Monitoring System (HMS) would allow prevention by either a corrective action or shifting to manual control. This invention is based on continuous glucose monitoring (CGM) data that provides a reliable layer of protection to insulin therapy, and provides a Glucose Rate Increase Detector (GRID) for the use with CGM Systems, Insulin pumps and the Artificial Pancreas (AP) for the detection of rises in glucose associated with meal events and for triggering of safe meal boluses.

The GRID is a module of the HMS that has been designed as a component of the AP that operates in parallel to the controller. The objective of the GRID is to detect persistent increases in glucose associated with a meal, and either trigger a meal bolus to blunt the meal peak safely (during closed-loop control) or alert the subject to bolus for a meal (open-loop control). It may be used in open-loop control, closed-loop control with user input, or fully automatic closed-loop control.

The invention GRID provides a safety system that can accompany insulin pumps and continuous glucose monitoring systems, as well as artificial pancreas. The invention can be used to improve CGM capabilities in detecting meal disturbances and recommending correction boluses to provide better glycemic control, including less time in hyperglycemia.

In one aspect the invention provides a GRID for use in an artificial pancreas (AP), wherein the GRID detects in a person persistent increases in glucose associated with a meal, and either triggers a meal bolus to blunt meal peak safely, during closed-loop control, or alerts the person to bolus for a meal, during open-loop control.

In embodiments the GRID comprises a GRID algorithm which uses CGM data to estimate the rate of change (ROC) of glucose and detect meal-related glucose excursions, the algorithm comprising: a) a pre-processing section to prepare the CGM data for analysis, b) an estimation section to approximate the ROC of glucose, and c) a detection section to logically pinpoint meal events.

In embodiments: a) in the pre-processing section, the algorithm filters the CGM data using a noise-spike filter; b) in the estimation section, the ROC of glucose is calculated using the first derivative of a 3-point Lagrangian interpolation polynomial, evaluated at the most recent point; and/or, c) the detection section comprises a logic wherein the detection is positive and equal to 1 at the current point only if a corresponding filtered point is above a value ($G_{min}$) chosen large enough to isolate post-meal glucose values and to avoid the hypoglycemia region, and either the last three ROC values are above $G_{min}$ or the last two are above $G_{min}$, wherein the ROC cutoffs are chosen to isolate post-meal rises, and provides a hierarchical approach, with either two at a higher ROC or three at a lower ROC, which allows faster detection with higher ROC values.

In another aspect the invention provides a GRID configured to provide the steps of FIG. 1.

In another aspect the invention provides a HMS for real-time prediction of pending adverse events based on CGM data, comprising a subject GRID and a controller, which provides prevention of the events by either a corrective action or shifting to manual control.

In another aspect the invention provides a method for providing a reliable layer of protection to insulin therapy, comprising detecting rises in glucose associated with meal events and triggering safe meal boluses, wherein the detecting and triggering steps are performed with a subject GRID with a CGM system, an insulin pump or an artificial pancreas (AP).

In another aspect the invention provides an artificial pancreas programmed and configured to implement the protocol of FIG. 2.

The invention also provides corresponding algorithms for programming controllers, HMS, and APs to effectively implement the disclosed steps.

The invention also provides a method comprising directing and optionally, delivering, insulin delivery using a subject GRID, controller, HMS or AP.

The invention includes algorithms and insulin directing systems essentially as described herein, and all combinations of the recited particular embodiments. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

DESCRIPTION OF PARTICULAR EMBODIMENTS OF THE INVENTION

Figure 1:
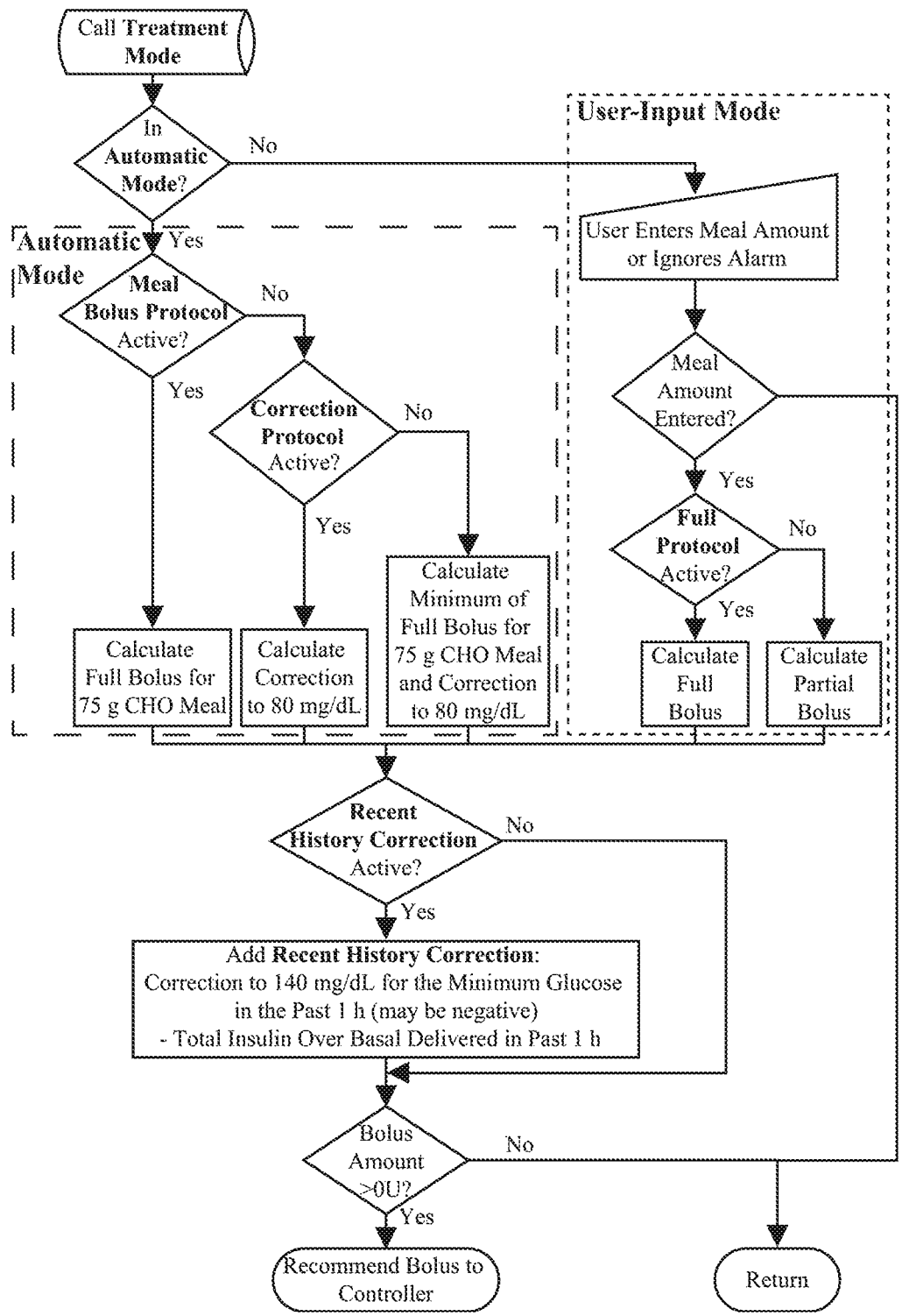
FIG. 1: Flow chart for GRID treatment protocols, followed after a meal is detected.

Design of the Glucose Rate Increase Detector: Summary.

The Glucose Rate Increase Detector (GRID), a module of the Health Monitoring System (HMS), has been designed to operate in parallel to the glucose controller to detect meal events and safely trigger a meal bolus.

The GRID algorithm was tuned on clinical data with 40-70 g CHO meals and tested on simulation data with 50-100 g CHO meals. Active closed and open-loop protocols were executed in silico with various treatments, including automatic boluses based on a 75 g CHO meal and boluses based on simulated user input of meal size. An optional function was used to reduce the recommended bolus using recent insulin and glucose history.

For closed-loop control of a three-meal scenario (50, 75 and 100 g CHO), the GRID improved median time in the 80-180 mg/dL range by 17% and in the >180 range by 14% over unannounced meals, using an automatic bolus for a 75 g CHO meal at detection. Under open-loop control of a 75 g CHO meal, the GRID shifted the median glucose peak down by 73 mg/dL and earlier by 120 min and reduced the time >180 mg/dL by 57% over a missed-meal bolus scenario, using a full meal bolus at detection.

The GRID improved closed-loop control in the presence of large meals, without increasing late postprandial hypoglycemia. Users of basal-bolus therapy could also benefit from GRID as a safety alert for missed meal corrections.

Methods

The modules of the HMS are each designed to monitor a specific component of the AP, or type of adverse event or disturbance seamlessly without interference. The most prevalent and risky occurrence is hypoglycemia. Thus, the Low Glucose Predictor (LGP) was designed to predict and prevent severe hypoglycemia in parallel to a controller, and has been shown to be effective in clinic in combination with the zone-Model Predictive Control (zone-MPC) controller.[22-24]

In an automatically controlled system, unmeasured disturbances such as meals can cause large excursions out of the target zone, leading to hyperglycemia and, often, subsequent hypoglycemia due to over-delivery in response to a meal. The GRID has been designed as the second module in the HMS, for the express purpose of detecting meal excursions with high specificity and short reaction time.

HMS with GRID Design

The GRID algorithm uses CGM data to estimate the rate of change (ROC) of glucose and detect meal-related glucose excursions. The GRID consists of three main subsections: 1) a pre-processing section to prepare the CGM data for analysis, 2) an estimation section to approximate the ROC of glucose, and 3) a detection section to logically pinpoint meal events.

In the pre-processing section, the algorithm filters the data using a noise-spike filter:[25]

$$G_{F,NS}(k) = \begin{cases} G_m(k) & \text{if } |G_m(k) - G_{F,NS}(k-1)| \le \Delta G \\ G_{F,NS}(k-1) - \Delta G & \text{if } (G_{F,NS}(k-1) - G_m(k)) > \Delta G \\ G_{F,NS}(k-1) + \Delta G & \text{if } (G_m(k) - G_{F,NS}(k-1)) > \Delta G \end{cases} \quad (0)$$

where k is the sampling instant, $G_{F,NS}$ (k−1) is the previous filtered value from the noise spike filter, $G_{F,NS}$ (k) is the filtered value resulting from the noise-spike filter, $G_m$ (k) is the measurement, and $\Delta G$ is the maximum allowable ROC, set to 3 mg/dL in a one-minute period, to limit the ROC to a physiologically-probable value.[26, 27] The data are then passed through a low pass filter to damp high frequency fluctuations:[25]

$$G_F(k) = \frac{\Delta t}{\tau_F + \Delta t} G_{F,NS}(k) + \left(1 - \frac{\Delta t}{\tau_F + \Delta t}\right) G_F(k-1), \qquad (0)$$

where $\Delta t$ is the sampling period, $\tau_F$ is the filter time constant, and $G_F$ is the filtered value. The value for $\tau_F$ has been tuned to smooth the data without introducing a long delay to optimize the specificity and detection speed of the algorithm.

In the estimation section, the ROC of glucose is calculated using the first derivative of the 3-point Lagrangian interpolation polynomial, evaluated at the most recent point, as follows:[18, 22]

$$G'_F(k) \cong \frac{t(k) - t(k-1)}{(t(k-2) - t(k-1))(t(k-2) - t(k))} G_F(k-2) + \\ \frac{t(k) - t(k-2)}{(t(k-1) - t(k-2))(t(k-1) - t(k))} G_F(k-1) + \\ \frac{2t(k) - t(k-2) - t(k-1)}{(t(k) - t(k-1))(t(k) - t(k-2))} G_F(k). \qquad (0)$$

In the detection logic, the detection, $GRID^+$, is positive (equal to 1) at the current point only if the filtered point is above a value $G_{min}$ and (ˆ) either the last three ROC values are above $G'_{min,3}$ or (∨) the last two are above $G'_{min,2}$:

$$GRID^+ = \begin{cases} 1 & \text{if } G_F(k) > G_{min} \wedge ((G'_F(k-2:k) > G'_{min,3}) \vee (G'_F(k-1:k) > G'_{min,2})) \\ 0 & \text{otherwise} \end{cases} \qquad (0)$$

The value of $G_{min}$ is chosen large enough to isolate post-meal glucose values and to avoid the hypoglycemia region. The ROC cutoffs are chosen to isolate post-meal rises and the hierarchical approach (with either two at a higher ROC or three at a lower ROC) allows faster detection with higher ROC values.

Kalman Filter Algorithm

A standard Kalman Filter (KF) was used as a benchmark to evaluate the GRID algorithm. The KF was a version of the Optimal Estimation algorithm used by Palerm, et al.[28], modified for use with 5 min sampling. The detection logic was implemented as it was in the GRID, and tuned along with the number of states (two states including glucose value and rate of change of glucose and three states including the acceleration of glucose as well) and the Q to R ratio for specificity and detection speed, resulting in slightly different tuning than the GRID.

Integration of HMS into Control Scheme

The knowledge of a meal event is helpful for disturbance rejection, and can be used as a form of inferential control. Using GRID, the state of the system, with respect to meal events, is estimated. Once the discrete meal event is detected by the GRID module, a sequence of events to reject the disturbance is activated. There are two modes explored in this paper, as shown in FIG. 1: The User-Input Mode, in which the detection triggers an alert that requests meal information, which is then used to deliver a full or partial meal bolus; and the Automatic Mode, in which a medium-sized meal bolus or a correction to low normal glucose levels is calculated and delivered automatically. Both modes can operate with the Recent History Correction (RHC) function active to adjust the recommended bolus. The RHC has two functions: 1) to calculate the insulin delivery over the last 60 min and subtract the amount over basal from the recommended bolus, and 2) to calculate a correction to 140 mg/dL for the lowest glucose value in the past 60 min and add it to the recommended bolus. The correction to 140 mg/dL can be negative, reducing the recommended bolus if recent glucose values were on the lower end of the target zone. This action provides an additional safeguard against over-delivery. All of these calculations are based on the clinical parameters of the subjects, including insulin to carbohydrate ratios and correction factors.

Figure 2:
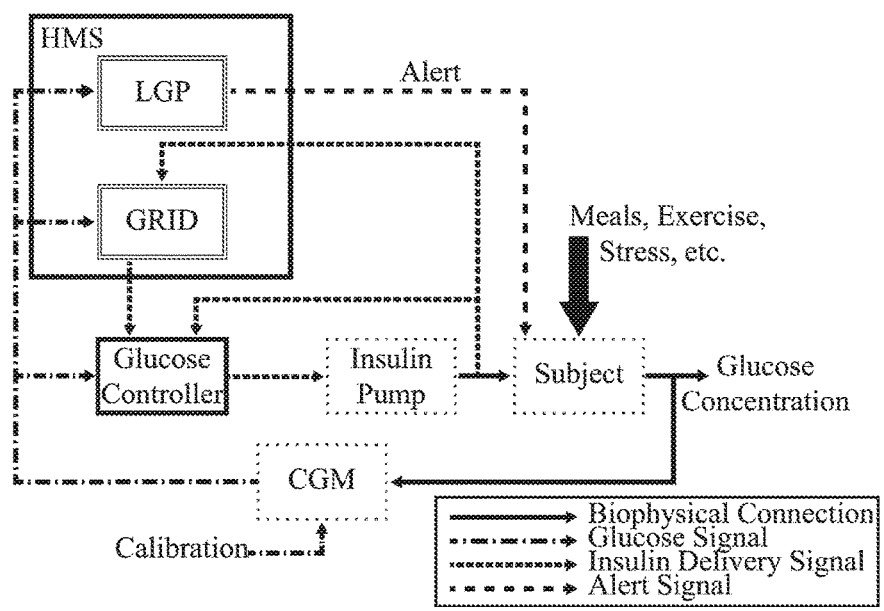
FIG. 2: Block diagram of a fully-automated AP with the GRID receiving CGM and insulin delivery information, and, upon detection of a meal, relaying a bolus recommendation to the Glucose Controller.

The full incorporation of the HMS, including the GRID and the LGP is shown in FIGS. 1 and 2, with CGM information being sent to both LGP and GRID, and insulin information being sent to GRID to allow for calculation of the RHC. The HMS operates in parallel with the controller to minimize interference and also to reduce the likelihood of adverse safety events due to module failure.

Training and Validation

The GRID and KF algorithms were tuned using training data from clinical trials and tested on a validation set of clinical data and an in silico data set, all with unannounced meals. As mentioned above, the algorithms were tuned, in order of importance, for low detection time, low false positive rate (high specificity), and high number of meals positively identified. Study details from all trials are shown in Table 1, with further results detailed in several references.[29-32]

Retrospective Clinical Data

The training data was comprised of 12 fully closed-loop, 24-h trials with subjects with T1DM using zone-MPC with a target zone of 80-140 mg/dL and HMS with LGP, performed at the Sansum Diabetes Research Institute using the Artificial Pancreas System (APS©).[33] The subjects were given small to medium-sized meals (40-50 g CHO) and performed 30 min of moderate exercise, with some subjects receiving 16 g CHO snacks before exercise, and several receiving 16 g rescue CHO per the HMS. All subjects used Dexcom® SEVEN® PLUS, (Dexcom® San Diego, Calif.) CGMs with a 5 min sampling period, and received subcutaneous insulin delivery.

After tuning the algorithms, validation was performed on data from a separate set of clinical trials with different subjects, all with T1DM.[34] Again, zone-MPC with HMS was used in the AP system. Subjects consumed meals of 40-70 g CHO and several received 16 g rescue CHO per the HMS.

In Silico Trial Testing

To further compare sets of tuning parameters, in silico trials were conducted using the Food and Drug Administration (FDA)-accepted UVA/Padova metabolic simulator consisting of 10 adult subjects. The simulation was started at 3:00 am and closed-loop control using zone-MPC with Insulin-on-board (IOB) input constraints was initiated at 5:00 am. The zone-MPC target glucose zones were 80-140 mg/dL from 7:00 am to 10:00 pm and 110-170 mg/dL from midnight to 5:00 am, with smooth transitions in between.[24] Meals of 50, 75, and 100 g were given at 7:00 am, 1:00 pm, and 6:00 pm, respectively, with control continuing until 3:00 am the next day. Data were collected using a sampling time of 1 min and tested using the GRID and KF algorithms after down-sampling to 5 min.

Cost-Benefit Analysis

The success of automatically rejecting the meal disturbance is highly dependent on the speed of detection. If detected too late, it may be of no use, or even cause hypoglycemia if too much insulin is delivered in excess of the controller correction. The simulator provides a sampling period of 1 min, so an analysis of the benefit of faster sampling rate on speed of detection, rise at detection, and the percentage of meals detected was performed.

Prospective Application

Several in silico scenarios with GRID actively running and triggering meal boluses were performed to test the algorithm. All scenarios used a sampling period of 5 min Standard Care Alert For subjects on standard basal-bolus therapy, meal boluses are sometimes missed, especially by adolescents or busy adults.[35] A missed meal bolus during standard basal-bolus therapy was simulated, to evaluate the ability of the algorithm to inform a CGM user of the missed bolus in a timely manner, blunting the glucose peak and decreasing the time in hyperglycemia. An 18 h scenario with a 50, 75, or 100 g CHO meal at 4.5 h was simulated with several protocols, shown in Table 2. User-input boluses are delivered at the cycle after detection to simulate the delay of waiting for user response.

Zone-MPC with Inferential Control

As shown above, the GRID was integrated into the control scheme as a form of inferential control, by detecting the meal disturbance, calculating an insulin bolus to reject the disturbance, and feeding this information to the zone-MPC controller. The LGP module of the HMS was also active, with a prediction threshold of 65 mg/dL and an activation threshold of 100 mg/dL.[22, 23, 36, 37] A 24 h scenario with three meals of 50, 75, and 100 g CHO was performed, as above in the CHO per the HMS.

In Silico Trial Testing section. Control protocols are shown in

Table 3.

Results and Discussion: Training and Validation

Figure 3:
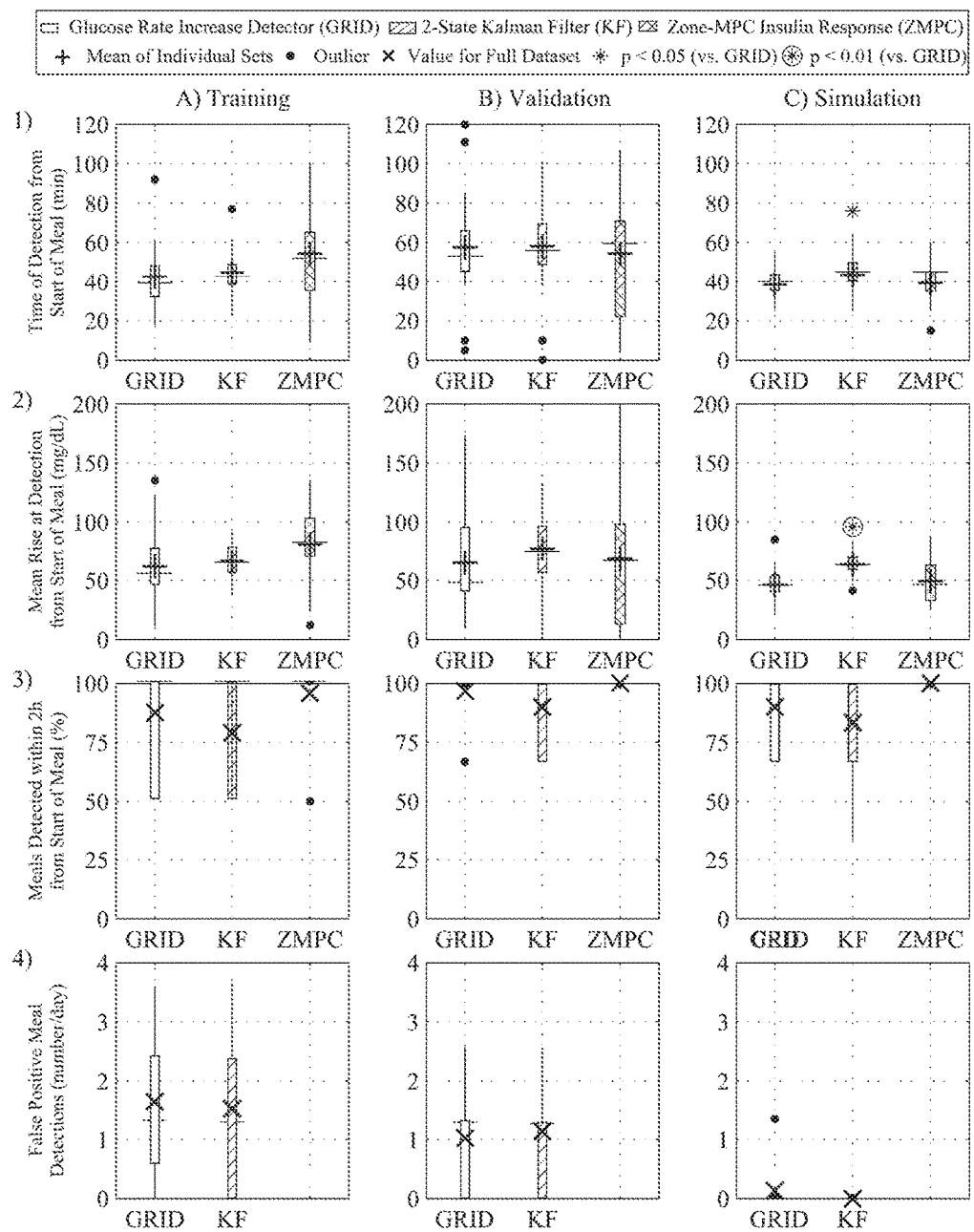
FIG. 3: Results for the GRID and Kalman Filter (KF), compared with the zone-MPC insulin response.

Based on the training data, the best set of tuning parameters for the GRID was the following: $\tau=6$ min, $G_{min}=130$ mg/dL, $G'_{min,2}=1.5$ mg/dL/min, and $G'_{min,2}=1.6$ mg/dL/min. This combination of parameters resulted in a mean time to detection of 42 min from the start of the meal, 87.5% of meals detected within 2 h, and 1.6 false positive detections per day. Due to the large number of snacks and hypoglycemia rescues, adjusted values for meals detected and false positive alarms were calculated, resulting in 65% of all carbohydrate ingestions being detected and only 0.58 false positive detections per day. For KF, the best set of tuning parameters was a two-state estimate with Q:R=0.1, $G_{min}=140$ mg/dL, $G'_{min,3}=1.75$ mg/dL/min, and $G'_{min,2}=1.85$ mg/dL/min. The mean time to detection was 45 min from the start of the meal, 79.2% of meals were detected within 2 h, and 1.5 false positive detections occurred per day. The adjusted calculation resulted in 57% of all carbohydrate ingestions being detected and only 0.58 false positive detections per day. Both algorithms were compared to the insulin response by the controller, quantified as the time from the start of the meal to the time when the average delivery over 15 min was more than 50% above the basal rate. The insulin response was compared because, depending on the glucose values and trend at meal time, and the subject's sensitivity to CHO and insulin, some meals did not result in a pronounced excursion. In these cases, a positive meal detection alert is not expected or necessary. In both validation and simulation, both algorithms performed with higher detection rates and lower false positive rates than in the training set. In simulation, detection was faster for the GRID. Results of GRID and KF on the training, validation, and simulation data are shown in FIG. 3, with paired t-test results comparing GRID to KF shown above the boxes with asterisks or circled asterisks when statistically significant.

Cost-Benefit Analysis

Figure 4:
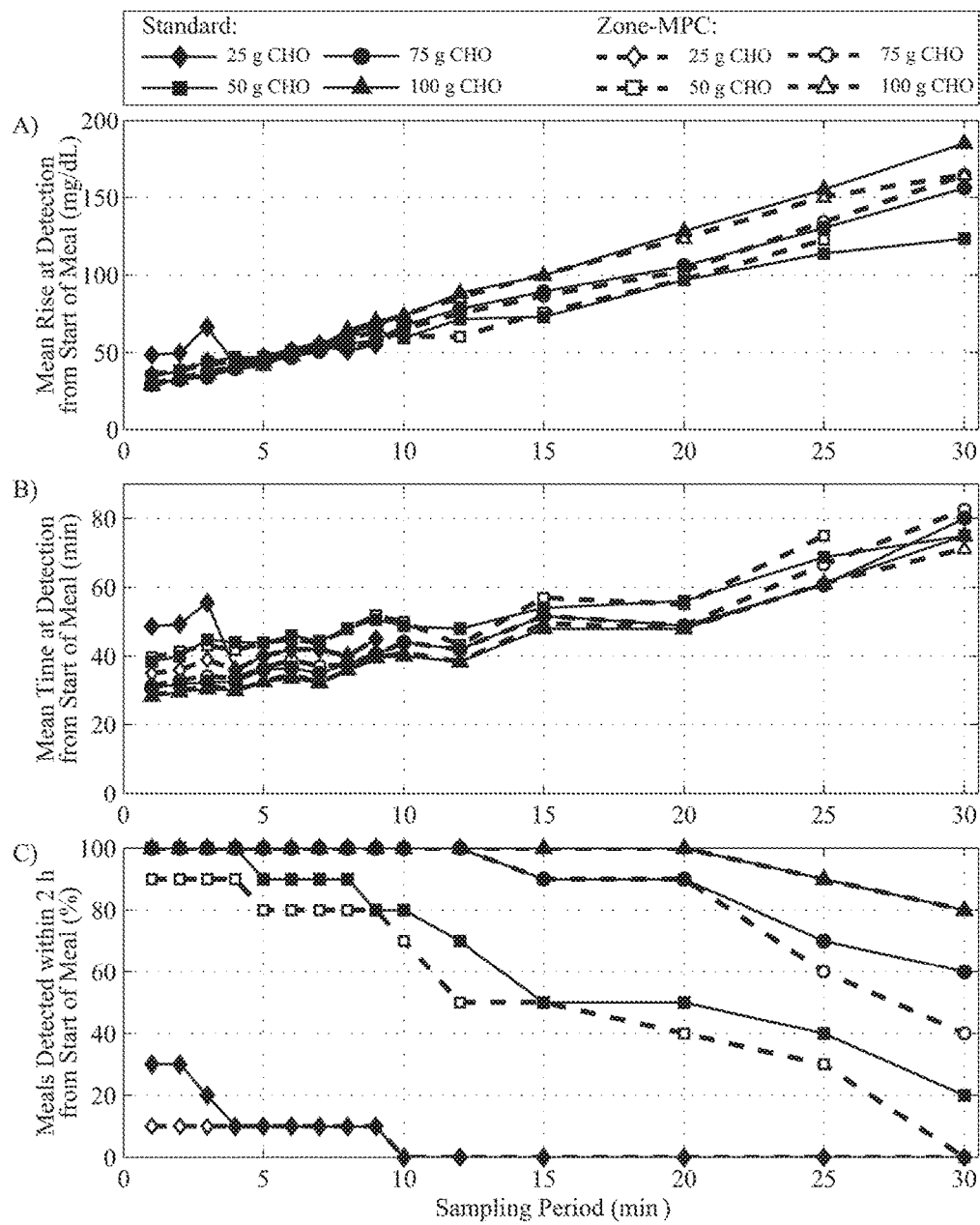
FIG. 4: Results of a cost-benefit analysis of sampling period on meal detection metrics using in silico data.

The cost of faster sampling can be seen in the form of expensive sensors and increased energy consumption by the sensors, receivers, and controllers, which could lead to shorter life and increased monetary cost. As the glucose sampling period increases, it is expected that detection of meals will deteriorate, so faster sampling period could improve the performance of a controller with inferential control using meal detection. The cost-benefit analysis of this system was performed by testing sampling times of 1 to 30 min, as seen in FIG. 4. For meals above 50 g CHO, a 5 min increase in time to detection and a 15 mg/dL increase in glucose at detection resulted when increasing from 1 to 5 min sampling, while all meals were still detected. Metrics for smaller meals were more impacted, due to a less pronounced glucose excursion. Small meals can generally be dealt with without the use of additional insulin from meal detection. This result indicates that a sampling period of 5 min is sufficient for meal detection of medium to large meals but, if reliable 1 min sampling was readily and cheaply available, meal detection could be improved.

Prospective Application; Standard Care Alert

The GRID yielded positive meal detections approximately 40-45 min from the start of meals, and reduced both the meal peaks and the duration of hyperglycemia, when compared to unannounced meals. The result of the delay in the bolus during GRID-active protocols is a large improvement over the missed meal protocol (B).

Figure 5:
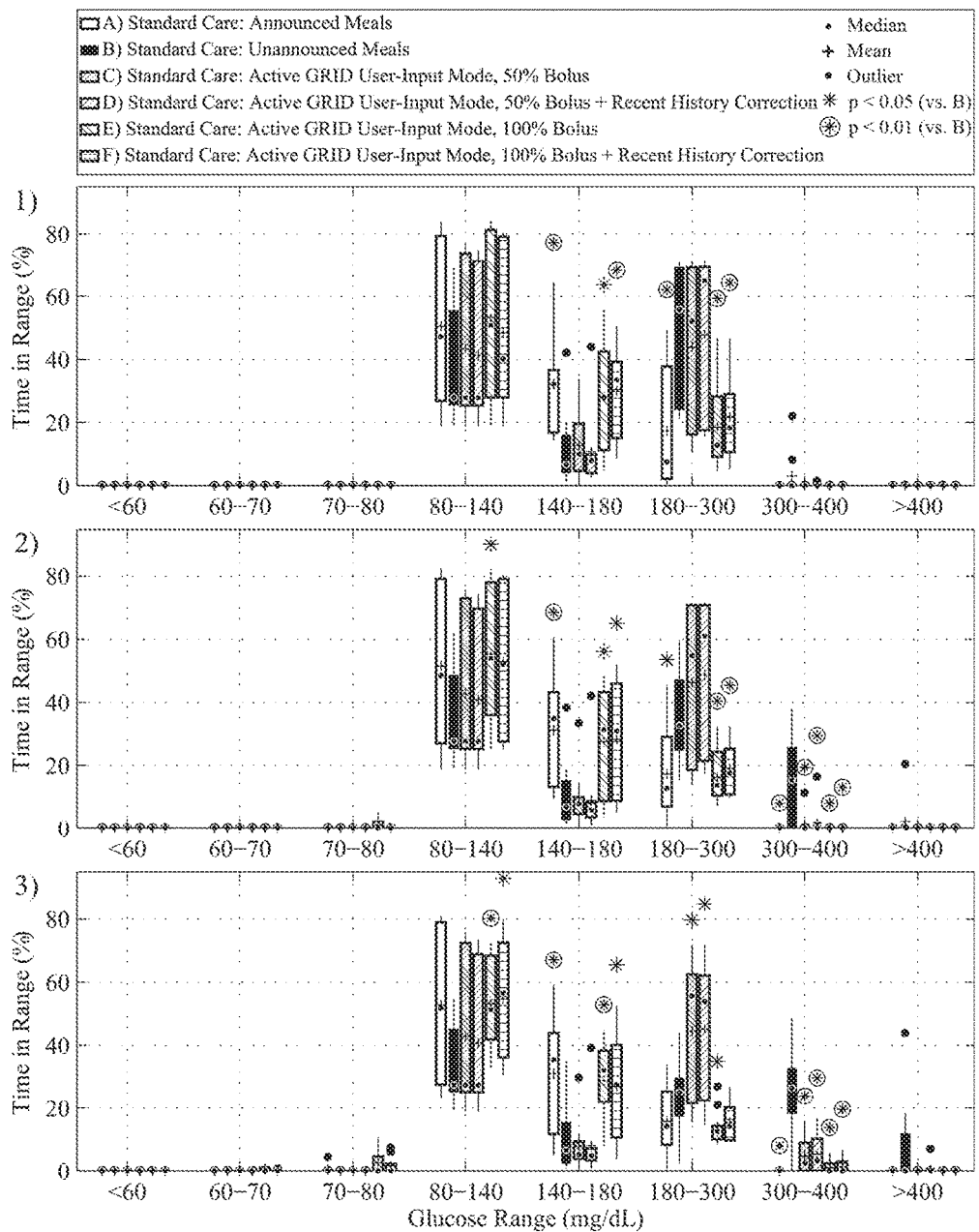
FIG. 5: Time in range results of an 18 h study of adult subjects using the UVA/Padova simulator with CHO meal at 4.5 h.

The time in range results of single meals of 50, 75, or 100 g CHO with open-loop therapy are shown in FIG. 5, with paired t-test results comparing the unannounced protocol (B) to the others shown above the boxes with asterisks or circled asterisks when statistically significant. In the case of open-loop control, a full bolus with RHC is recommended at detection (E), with significantly better time in range and much less time in the hyperglycemia range than the unannounced protocol (B).

Zone-MPC with Inferential Control

Figure 6:
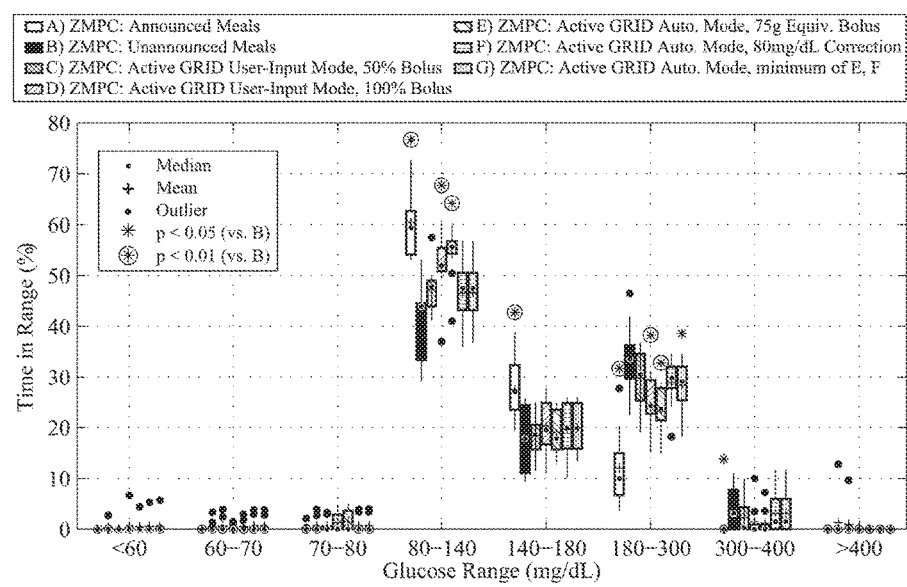
FIG. 6: Time in range results of a 24 h in silico study of 10 adult subjects using the UVA/Padova simulator with CHO meals.

Detailed results of the zone-MPC protocols were determined, with time in range in FIG. 6. The GRID yielded positive meal detections approximately 40-45 min from the start of the meal, and delivered a calculated bolus, as described above. For the Automatic Mode bolus protocol (E), the meal peak and time in the 80-180 range were significantly better than in the unannounced case (B). For all meals, the time in the 80-180 range was improved over the unannounced protocol (B) by both the Automatic Mode bolus protocol (E), and User-Input Mode protocol (D). Although up to five hypoglycemia treatments were given per HMS with LGP, seven out of ten subjects had no hypoglycemia (<70 mg/dL), and the number of treatments and time under 70 mg/dL was not significantly higher for any of the protocols when compared to announced meals. In the case of closed-loop control, a full bolus for a 75 g CHO meal with RHC is recommended at detection (E), with significantly better time in range and much less time in the hyperglycemia range than the unannounced protocol (B). Detailed results are shown in Table 4.

CONCLUSIONS

The GRID module of the HMS was designed to accurately and quickly identify meal glucose excursions and logically recommend an insulin bolus to reject the meal disturbance. The algorithm was tuned using noisy clinical trial data with unannounced meals and several snacks, and the same controller used in the simulations. It should be noted that, while tuning for speed of detection was the first priority, any algorithms that produced more than 2.0 false positive detections per day were excluded. Even with those algorithms included, the fastest detection time would have been 35 min for KF or GRID. Thus, with controlled data and medium-sized meals, a 30+ min delay for meal detection based on CGM data is the limit of detection speed.

The GRID is designed as a parallel module to the controller that focuses on meal detection, to trigger a rejection of the meal disturbance. This approach provides a more bolus-like meal response by the controller, and the IOB constraint keeps over-delivery from occurring, essentially front-loading the insulin for the meal response without need for outside input. With the knowledge that the meal detection is delayed by at least 30 min, the disturbance rejection action was logically modified with by the RHC function, which reduced the recommended bolus by recent delivery and adjusted for recent glucose history.

During closed-loop control, the GRID was able to improve control in the presence of large meals, without increasing the instances of hypoglycemia or increasing the time in the hypoglycemia range (<70 mg/dL), as seen in FIG. 6 and Table 4. In addition, fast recognition of missed meal boluses in open-loop mode, for users on standard therapy can greatly improve the time in range and serve as a safety alert for users of the currently available devices.

LEGENDS TO THE FIGURES

FIG. 1: Flow chart for GRID treatment protocols, followed after a meal is detected. Automatic Mode protocols are in the box surrounded by a dashed line and User-Input Mode protocols are in the box surrounded by the dotted line.

FIG. 2: Block diagram of a fully-automated AP with the GRID receiving CGM and insulin delivery information, and, upon detection of a meal, relaying a bolus recommendation to the Glucose Controller. The HMS is outlined in a black solid line, with sub-modules GRID and LGP outlined in double lines, the controller in black solid and physical devices and the subject in dotted lines.

FIG. 3: Results for the GRID (no fill) and KF (45 degree lines), compared with the zone-MPC insulin response (45 degree cross hatches). (A) Training set from a 12-subject clinical trial using zone-MPC with two unannounced meals (50 and 40 g CHO); (B) Validation set from a 10-subject clinical trial using zone-MPC, with three unannounced meals (70, 40, and 70 g CHO); and (C) Simulation set from a 10-subject scenario, with three unannounced meals (50, 75, and 100 g CHO). (1) Time of detection; (2) rise in glucose at detection; (3) the percentage of meals that were detected within 2 h; (4) rate of false positive detections. The metrics with statistically significantly different results from the GRID algorithm (paired t-test, $p<0.05$ and $p<0.01$) are shown above the boxes with asterisks and circled asterisks, respectively. Means are shown as crosses and totals in x's.

FIG. 4: Results of a cost-benefit analysis of sampling period on meal detection metrics using in silico data. Meals of 25, 50, 75, or 100 g CHO with no bolus are shown in diamonds, squares, circles, and triangles, respectively. Both Zone-MPC, shown in dotted lines with open symbols, or Standard Care (basal/bolus), shown with solid lines and filled symbols, control types were tested. The GRID was executed on the data with sampling periods varying from 1 to 30 min (A) Mean rise in glucose from meal commencement to time of detection; (B) mean time from meal commencement to time of detection; and (C) percent of meals detected within 2 h from the start of the meal.

FIG. 5: Time in range results of an 18 h in silico study of 10 adult subjects using the UVA/Padova simulator with, from top to bottom, 50 g (1), 75 g (2), or 100 g (3) CHO meal at 4.5 h. Scenarios (A-F) correspond to (A-F) in FIG. 5 and Table 2 in no fill, black fill, 45 degree cross hatches, 45 degree lines (from bottom left to top right), −45 degree lines (from top left to bottom right), and horizontal lines, respectively. Means are shown in black crosses, and medians in dots with white borders. Protocols that have statistically significantly different results from the unannounced (B) protocol (paired t-test, $p<0.05$ and $p<0.01$) are shown above the boxes with asterisks, *, and circled asterisks, ⊛, respectively.

FIG. 6: Time in range results of a 24 h in silico study of 10 adult subjects using the UVA/Padova simulator with 50, 75, and 100 g CHO meals at 7:00, 13:00, and 19:00, respectively. Scenarios (A-G) correspond to (A-G) in Table 3 in no fill, black fill, 45 degree cross hatches, 45 degree lines (from bottom left to top right), −45 degree lines (from top left to bottom right), horizontal lines, and vertical lines, respectively. Means are shown in black crosses, and medians in black dots with white borders. Protocols that have statistically significantly different results from the unannounced (B) protocol (paired t-test, $p<0.05$ and $p<0.01$) are shown above the boxes with asterisks, *, and circled asterisks, ⊛, respectively.

REFERENCES

1. The Diabetes Control and Complications Trial Research Group. The Effect of Intensive Treatment of Diabetes on the Development and Progression of Long-Term Complications in Insulin-Dependent Diabetes Mellitus. *N Engl J Med*. 1993; 329:977-986.
2. Bequette B W. Challenges and Recent Progress in the Development of a Closed-loop Artificial Pancreas. *Annu Rev Control*. December 2012; 36(2):255-266.
3. Brazeau A S, Mircescu H, Desjardins K, Leroux C, Strychar I, Ekoe J M, Rabasa-Lhoret R. Carbohydrate counting accuracy and blood glucose variability in adults with type 1 diabetes. *Diabetes Res Clin Pract*. January 2013; 99(1):19-23.
4. Shepard J A, Gonder-Frederick L, Vajda K, Kovatchev B. Patient perspectives on personalized glucose advisory systems for type 1 diabetes management. *Diabetes Technol Ther*. October 2012; 14(10):858-861.
5. van Bon A C, Kohinor M J, Hoekstra J B, von Basum G, deVries J H. Patients' perception and future acceptance of an artificial pancreas. *J Diabetes Sci Technol*. May 2010; 4(3):596-602.
6. Weinzimer S A, Shen J L, Cengiz E, Kim G, Ruiz J L, Carria L, Voskanyan G, Roy A, Tamborlane W V. Effect of pramlintide on prandial glycemic excursions during closed-loop control in adolescents and young adults with type 1 diabetes. *Diabetes Care*. October 2012; 35(10): 1994-1999.
7. Steil G M, Palerm C C, Kurtz N, Voskanyan G, Roy A, Paz S, Kandeel F R. The effect of insulin feedback on closed loop glucose control. *J Clin Endocrinol Metab*. May 2011; 96(5):1402-1408.
8. Dassau E, Zisser H, Harvey R A, Percival M W, Grosman B, Bevier W, Atlas E, Miller S, Nimri R, Jovanovič L, Doyle III F J. Clinical Evaluation of a Personalized Artificial Pancreas. *Diabetes Care*. 2013; 36(4):801-809.
9. Elleri D, Allen J M, Biagioni M, Kumareswaran K, Leelarathna L, Caldwell K, Nodale M, Wilinska M E, Acerini C L, Dunger D B, Hovorka R. Evaluation of a portable ambulatory prototype for automated overnight closed-loop insulin delivery in young people with type 1 diabetes. *Pediatr Diabetes*. September 2012; 13(6):449-453.
10. Cobelli C, Renard E, Kovatchev B P, Keith-Hynes P, Ben Brahim N, Place J, Del Favero S, Breton M, Farret A, Bruttomesso D, Dassau E, Zisser H, Doyle F J, 3rd, Patek S D, Avogaro A. Pilot studies of wearable outpatient artificial pancreas in type 1 diabetes. *Diabetes Care*. September 2012; 35(9):e65-67.
11. Breton M, Farret A, Bruttomesso D, Anderson S, Magni L, Patek S, Dalla Man C, Place J, Demartini S, Del Favero S, Toffanin C, Hughes-Karvetski C, Dassau E, Zisser H, Doyle F J, 3rd, De Nicolao G, Avogaro A, Cobelli C, Renard E, Kovatchev B, on behalf of The International Artificial Pancreas Study G. Fully Integrated Artificial Pancreas in Type 1 Diabetes: Modular Closed-Loop Glucose Control Maintains Near Normoglycemia. *Diabetes*. September 2012; 61(9):2230-2237.
12. McCall A L, Farhy L S. Treating type 1 diabetes: from strategies for insulin delivery to dual hormonal control. *Minerva Endocrinol*. June 2013; 38(2):145-163.
13. Lane J E, Shivers J P, Zisser H. Continuous glucose monitors: current status and future developments. *Curr Opin Endocrinol Diabetes Obes*. April 2013; 20(2):106-111.
14. Renard E, Place J, Cantwell M, Chevassus H, Palerm C C. Closed-loop insulin delivery using a subcutaneous glucose sensor and intraperitoneal insulin delivery: feasibility study testing a new model for the artificial pancreas. *Diabetes Care*. January 2010; 33(1):121-127.
15. Hovorka R, Kumareswaran K, Harris J, Allen J M, Elleri D, Xing D Y, Kollman C, Nodale M, Murphy H R, Dunger D B, Amiel S A, Heller S R, Wilinska M E, Evans M L. Overnight closed loop insulin delivery (artificial pancreas) in adults with type 1 diabetes: crossover randomised controlled studies. *Brit Med J*. April 2011; 342.
16. Bruttomesso D, Farret A, Costa S, Marescotti M C, Vettore M, Avogaro A, Tiengo A, Dalla Man C, Place J, Facchinetti A, Guerra S, Magni L, De Nicolao G, Cobelli C, Renard E, Maran A. Closed-Loop Artificial Pancreas Using Subcutaneous Glucose Sensing and Insulin Delivery and a Model Predictive Control Algorithm: Preliminary Studies in Padova and Montpellier. *J Diabetes Sci Technol*. 2009; 3(5):1014-1021.
17. Nimri R, Atlas E, Ajzensztejn M, Miller S, Oron T, Phillip M. Feasibility study of automated overnight closed-loop glucose control under MD-logic artificial pancreas in patients with type 1 diabetes: the DREAM Project. *Diabetes Technol Ther*. August 2012; 14(8):728-735.
18. Dassau E, Bequette B W, Buckingham B A, Doyle III F J. Detection of a Meal Using Continuous Glucose Monitoring (CGM): Implications for an Artificial β-cell. *Diabetes Care*. 2008; 31(2):295-300.
19. Cameron F, Niemeyer G, Buckingham B A. Probabilistic Evolving Meal Detection and Estimation of Meal Total Glucose Appearance. *J Diabetes Sci Technol*. 2009; 3(5): 1022-1030.
20. Lee H, Buckingham B A, Wilson D M, Bequette B W. A Closed-Loop Artificial Pancreas Using Model Predictive Control and a Sliding Meal Size Estimator. *J Diabetes Sci Technol*. 2009; 3(5):1082-1090.
21. Dassau E, Herrero P, Zisser H, Buckingham B A, Jovanovič L, Dalla Man C, Cobelli C, Vehí J, Doyle III F J Implications of Meal Library & Meal Detection to Glycemic Control of Type 1 Diabetes Mellitus through MPC Control. *Proc 17th IFAC World Congress*. Seoul, Korea 2008:4228-4233.
22. Harvey R A, Dassau E, Zisser H, Seborg D E, Jovanovič L, Doyle III F J. Design of the Health Monitoring System for the Artificial Pancreas: Low Glucose Prediction Module. *J Diabetes Sci Technol*. November 2012.
23. Harvey R A, Dassau E, Bevier W, Seborg D E, Jovanovič L, Doyle III F J, Zisser H. Clinical Evaluation of an Automated Artificial Pancreas Using Zone-Model Predictive Control and Health Monitoring System. *Diabetes Technol. & Ther.(submitted)*. 2013.
24. Gondhalekar R, Dassau E, Zisser H, Doyle III F J. Periodic-Zone Model Predictive Control for Diurnal Closed-loop Operation of an Artificial Pancreas. *Diabetes Science and Technology*. 2013; Submitted.
25. Seborg D E, Edgar T F, Mellichamp D A, Doyle III F J. *Process Dynamics and Control*. 3rd ed. Hoboken, N.J.: John Wiley & Sons; 2011.
26. Dunn T C, Eastman R C, Tamada J A. Rates of Glucose Change Measured by Blood Glucose Meter and the GlucoWatch Biographer During Day, Night, and Around Mealtimes. *Diabetes Care*. September 2004; 27(9):2161-2165.
27. Rahaghi F N, Gough D A. Blood glucose dynamics. *Diabetes Technol Ther*. April 2008; 10(2):81-94.
28. Palerm C C, Willis J P, Desemone J, Bequette B W. Hypoglycemia prediction and detection using optimal estimation. *Diabetes Technol Ther*. February 2005; 7(1): 3-14.
29. Zisser H C, Dassau E, Bevier W, Harvey R A, Jovanovič L, Doyle III F J. Clinical Evaluation of a Fully-Automated Artificial Pancreas using Zone-Model Predictive Control with Health Monitoring System. Paper presented at: American Diabetes Association 72nd Scientific Sessions, 2012; Philadelphia, Pa.
30. Lee J J, Zisser H C, Dassau E, Farret A, Place J, Pelletier M J, Harvey R A, Doyle III F J, Renard E. Clinical Results of Artificial Pancreas Using Intraperitoneal Insulin Delivery Paper presented at: American Diabetes Association 73nd Scientific Sessions, 2013; Chicago, Ill.
31. Harvey R A, Dassau E, Zisser H, Seborg D E, Jovanovič L, Doyle III F J. Clinical Evaluation of the Health Monitoring System (HMS). Paper presented at: 6th International Conference on Advanced Technologies and Treatments for Diabetes, 2013; Paris, Fr.
32. Dassau E, Lee J J, Renard E, Zisser H, Doyle III F J. Clinical and Engineering Aspects of IP Insulin Delivery in Closed Loop Study—The Diaport Experience. Paper presented at: 6th International Conference on Advanced Technologies and Treatments for Diabetes, 2013; Paris, FR.
33. Dassau E, Zisser H, Palerm C C, Buckingham B A, Jovanovič L, Doyle III F J. Modular Artificial β-Cell System: A Prototype for Clinical Research *J Diabetes Sci Technol.* 2008; 2(5):863-872.
34. Lee J J, Dassau E, Zisser H, Jovanovič L, Doyle III F J. Evaluation of Zone-MPC for Intraperitoneal Insulin Delivery. Paper presented at: American Diabetes Association 72nd Scientific Sessions, 2012; Philadelphia, Pa.
35. Olinder A L, Nyhlin K T, Smide B. Reasons for missed meal-time insulin boluses from the perspective of adolescents using insulin pumps: 'lost focus'. *Pediatr Diabetes.* June 2011; 12(4 Pt 2):402-409.
36. Grosman B, Dassau E, Zisser H C, Jovanovič L, Doyle III F J. Zone model predictive control: a strategy to minimize hyper- and hypoglycemic events. *J Diabetes Sci Technol.* July 2010; 4(4):961-975.
37. van Heusden K, Dassau E, Zisser H C, Seborg D E, Doyle III F J. Control-relevant models for glucose control using a priori patient characteristics. *IEEE Trans Biomed Eng.* July 2012; 59(7):1839-1849.

TABLE 2

Standard care alert simulation protocols.

| Protocol | Announced Meal | GRID Mode | GRID Protocol | Recent History Correction Active | Bolus Size (%) |
|---|---|---|---|---|---|
| A | Yes | Off | — | — | 100 |
| B | No | Off | — | — | 0 |
| C | No | User-Input | Partial | No | 50 |
| D | No | User-Input | Partial | Yes | 50 |
| E | No | User-Input | Full | No | 100 |
| F | No | User-Input | Full | Yes | 100 |

TABLE 1

Characteristics of training clinical datasets, validation clinical datasets, and simulation testing set. Zone-MPC with unannounced meals was used during each trial and simulation. Values after the number of males are presented as median (range) except where indicated. All ranges are calculated with CGM data.

| | A) Training | B) Validation | C) Simulation |
|---|---|---|---|
| N, datasets | 12 | 10 | 10 |
| Male sex, number | 4 | 7 | — |
| Age, y | 53 (28-62) | 52 (30-62) | — |
| Height, cm | 167 (157-193) | 170 (156-178) | — |
| Weight, kg | 70 (53-132) | 65 (54-94) | 72 (46-99) |
| Total Daily Basal, U | 18.4 (11.6-46.2) | 24 (7.5-39.5) | 29.7 (22-45.7) |
| Total Daily Insulin, U | 33 (22.9-73.2) | 38 (23.1-105) | 43 (34-72) |
| Default Carbohydrate Ratio, g CHO/U | 10.5 (6.33-15) | 11.5 (3.5-20) | 16.5 (9-22) |
| Hypoglycemia Treatments[a], g CHO | 56 (16-112) | 24 (0-112) | 0 (0-80) |
| Default Correction Factor, mg/dL/U | 51.5 (25-100) | 58 (12.5-70) | 42.5 (26-53) |
| Overall duration, h | 22 (19-24) | 24 (22-25) | 24 |
| Time <50 mg/dL, % | 0 (0-1.6) | 0 (0-14) | 0 (0-1.3) |
| Time <70 mg/dL, % | 2 (0-6.4) | 1.7 (0-20) | 0 (0-5.9) |
| Time 70-80 mg/dL, % | 2.5 (0.76-6.8) | 1.7 (0-13) | 0 (0-3.9) |
| Time 80-140 mg/dL, % | 46 (15-65) | 26 (15-41) | 44 (29-53) |
| Time 140-180 mg/dL, % | 22 (4.5-39) | 19 (6.8-25) | 18 (9.3-26) |
| Time 180-250 mg/dL, % | 18 (4.2-41) | 24 (7.1-45) | 26 (14-40) |
| Time >250 mg/dL, % | 7.6 (0-20) | 25 (4.6-53) | 9.5 (0-36) |
| Total Insulin Delivered, U | 22.3 (14.6-53.8) | 37.2 (14.7-56.2) | 35.8 (29.3-50.8) |
| Size of Meal 1, g CHO | 50 (50-51) | 70 (70-70) | 50 (50-50) |
| Baseline Glucose at Meal 1, mg/dL | 112 (63-204) | 108 (58-244) | 117 (98-139) |
| Time of Meal 1[a] | 19:25 ± 00:30 | 18:54 ± 00:08 | 7:00 |
| Peak Glucose after Meal 1, mg/dL | 218 (128-266) | 286 (217-366) | 229 (178-286) |
| Time of Peak Glucose after Meal 1, min[b] | 100 (60-115) | 113 (70-120) | 113 (77-120) |
| Size of Meal 2, g CHO | 40 (38-40) | 40 (40-40) | 75 (75-75) |
| Baseline Glucose at Meal 2, mg/dL | 111 (79-160) | 126 (67-185) | 116 (91-138) |
| Time of Meal 2[a] | 06:58 ± 00:08 | 07:52 ± 00:07 | 13:00 |
| Peak Glucose after Meal 2, mg/dL | 285 (176-378) | 269 (164-387) | 250 (219-423) |
| Time of Peak Glucose after Meal 2, min[b] | 91 (65-115) | 90 (75-115) | 107 (73-120) |
| Size of Meal 3, g CHO | — | 70 (70-70) | 100 (100-100) |
| Baseline Glucose at Meal 3, mg/dL | — | 150 (39-226) | 97 (70-141) |
| Time of Meal 3[a] | — | 12:52 ± 00:07 | 19:00 |
| Peak Glucose after Meal 3, mg/dL | — | 291 (83-401) | 310 (233-509) |
| Time of Peak Glucose after Meal 3, min[b] | — | 115 (60-120) | 111 (86-120) |

[a]mean ± standard deviation,
[b]Calculated as peak within 2 h of the start of the meals.

TABLE 3

Zone-MPC with inferential control simulation protocols.

| Protocol | Announced Meal | GRID Mode | GRID Protocol | Recent History Correction Active | Bolus Size (%) |
|---|---|---|---|---|---|
| A | Yes | Off | — | — | 100 |
| B | No | Off | — | — | 0 |
| C | No | User-Input | Partial | Yes | 50 |
| D | No | User-Input | Full | Yes | 100 |
| E | No | Automatic | 75 g CHO Meal Bolus | Yes | 100 |
| F | No | Automatic | Correction to 80 mg/dL | Yes | 100 |
| G | No | Automatic | Minimum of E and F | Yes | 100 |

Table 4: Characteristics of an in silico study of 10 adult subjects using the UVa/Padova simulator. Scenarios are A-G as described in

TABLE 3

| | A | B | C | D |
|---|---|---|---|---|
| Time <50 mg/dL, % | 0 (0-0) | 0 (0-1.3) | 0 (0-0) | 0 (0-4.5) |
| Time 50-70 mg/dL, % | 0 (0-0) | 0 (0-4.6) | 0 (0-3.8) | 0 (0-3.5) |
| Time 70-80 mg/dL, % | 0 (0-2.0) | 0 (0-3.9) | 0 (0-3.2) | 0 (0-4.9) |
| Time 80-180 mg/dL, % | 89 (72-96)⊖ | 57 (44-78) | 63 (53-81) | 73 (48-85)⊖ |
| Time >180 mg/dL, % | 9.9 (3.6-28)⊖ | 39 (22-51) | 34 (19-42) | 25 (15-39)⊖ |
| Time >250 mg/dL, % | 0 (0-0)⊖ | 9.5 (0-36) | 7.8 (0-30) | 3.6 (0-17) |
| Total Insulin Delivered, U | 40 (31-64) | 36 (29-51) | 37 (30-54) | 38 (30-60) |
| Hypoglycemia Treatments, g CHO | 0 (0-16) | 0 (0-80) | 0 (0-32) | 0 (0-64) |
| Size of Meal 1, g CHO | 50 | 50 | 50 | 50 |
| Baseline Glucose at Meal 1, mg/dL | 117 (98-139) | 117 (98-139) | 117 (98-139) | 117 (98-139) |
| Time of Meal 1 | 7:00 | 7:00 | 7:00 | 7:00 |
| Peak Glucose after Meal 1, mg/dL | 183 (148-197)⊖ | 229 (178-286) | 224 (178-283) | 221 (178-259) |
| Time of Peak Glucose from Start of Meal 1, min | 81.5 (53-116) | 113 (77-120) | 108 (77-120) | 104 (76-119) |
| Time 80-180 mg/dL from Start of Meal 1 to Meal 2% | 93 (75-100)⊖ | 58 (36-85) | 62 (44-85) | 73 (52-85) * |
| Glucose at Detection for Meal 1, mg/dL | 158 (147-173) | 159 (147-169) | 159 (147-169) | 159 (147-169) |
| Time of Detection from Start of Meal 1, min | 48 (45-55) | 43 (40-45) | 43 (40-45) | 43 (40-45) |
| Equivalent Meal Size for Bolus, g CHO | 50 | — | 11 (6.6-17) | 36 (32-42) |
| Size of Meal 2, g CHO | 75 | 75 | 75 | 75 |
| Baseline Glucose at Meal 2, mg/dL | 108 (95-123) | 116 (91-138) | 114 (91-139) | 105 (87-125) |
| Time of Meal 2 | 13:00 | 13:00 | 13:00 | 13:00 |
| Peak Glucose after Meal 2, mg/dL | 189 (161-222)⊖ | 250 (219-423) | 247 (216-421) | 235 (204-344) |
| Time of Peak Glucose from Start of Meal 2, min | 78.5 (58-120) | 107 (73-120) | 107 (72-119) | 99.5 (69-115) |
| Time 80-180 mg/dL from Start of Meal 2 to Meal 3% | 89 (67-100)⊖ | 42 (33-64) | 53 (39-71) | 64 (39-82)⊖ |
| Glucose at Detection for Meal 2, mg/dL | 149 (144-156) | 156 (152-198) | 153 (148-199) | 159 (147-188) |
| Time of Detection from Start of Meal 2, min | 40 (30-50) | 40 (30-55) | 40 (30-55) | 43 (30-55) |
| Equivalent Meal Size for Bolus, g CHO | 75 | — | 21 (3.3-31) | 57 (48-66) |
| Size of Meal 3, g CHO | 100 | 100 | 100 | 100 |
| Baseline Glucose at Meal 3, mg/dL | 96.5 (86-137) | 97 (70-141) | 92.5 (68-132) | 92 (84-199) |
| Time of Meal 3 | 19:00 | 19:00 | 19:00 | 19:00 |
| Peak Glucose after Meal 3, mg/dL | 215 (186-241)⊖ | 310 (233-509) | 294 (223-179) | 276 (223-397) |
| Time of Peak Glucose from Start of Meal 3, min | 75 (51-98) | 111 (86-120) | 101 (78-118) | 85.5 (64-102) |
| Time 80-180 mg/dL from Start of Meal 3 to end, % | 83 (60-96)⊖ | 52 (19-71) | 63 (44-75) | 71 (25-82) * |
| Glucose at Detection for Meal 3, mg/dL | 153 (144-163) | 172 (145-244) | 158 (150-209) | 165 (146-319) |
| Time of Detection from Start of Meal 3, min | 40 (25-50) | 40 (25-90) | 37 (25-45) | 40 (25-50) |
| Equivalent Meal Size for Bolus, g CHO | 100 | — | 31 (18-42) | 80 (64-89) |

| | E | F | G |
|---|---|---|---|
| Time <50 mg/dL, % | 0 (0-1.5) | 0 (0-2.6) | 0 (0-2.8) |
| Time 50-70 mg/dL, % | 0 (0-4.7) | 0 (0-5.6) | 0 (0-5.7) |
| Time 70-80 mg/dL, % | 0 (0-4.9) | 0 (0-3.9) | 0 (0-4.0) |
| Time 80-180 mg/dL, % | 74 (54-85)⊖ | 66 (46-82) | 66 (51-82) |
| Time >180 mg/dL, % | 25 (15-35)⊖ | 31 (18-42) * | 31 (18-40) * |
| Time >250 mg/dL, % | 4.7 (0-13) | 6.7 (0-20) | 6.7 (0-18) |
| Total Insulin Delivered, U | 38 (31-61) | 37 (30-54) | 37 (30-54) |
| Hypoglycemia Treatments, g CHO | 0 (0-64) | 0 (0-80) | 0 (0-64) |
| Size of Meal 1, g CHO | 50 | 50 | 50 |
| Baseline Glucose at Meal 1, mg/dL | 117 (98-139) | 117 (98-139) | 117 (98-139) |
| Time of Meal 1 | 7:00 | 7:00 | 7:00 |
| Peak Glucose after Meal 1, mg/dL | 212 (178-238) * | 222 (178-258) | 222 (178-258) |
| Time of Peak Glucose from Start of Meal 1, min | 89.5 (75-119) | 106 (77-120) | 106 (77-120) |
| Time 80-180 mg/dL from Start of Meal 1 to Meal 2% | 80 (56-90)⊖ | 68 (51-85) | 68 (51-85) |
| Glucose at Detection for Meal 1, mg/dL | 159 (147-169) | 159 (147-169) | 159 (147-169) |
| Time of Detection from Start of Meal 1, min | 13 (40-45) | 43 (40-45) | 43 (40-45) |
| Equivalent Meal Size for Bolus, g CHO | 63 (60-69) | 22 (15-29) | 22 (15-29) |
| Size of Meal 2, g CHO | 75 | 75 | 75 |
| Baseline Glucose at Meal 2, mg/dL | 94 (78-123) | 109 (91-124) | 109 (91-124) |
| Time of Meal 2 | 13:00 | 13:00 | 13:00 |

TABLE 3-continued

| | | | |
|---|---|---|---|
| Peak Glucose after Meal 2, mg/dL | 232 | (197-330) | 242 (212-361) | 242 (212-361) |
| Time of Peak Glucose from Start of Meal 2, min | 97 | (67-118) | 104 (71-120) | 104 (71-120) |
| Time 80-180 mg/dL from Start of Meal 2 to Meal 3% | 63 | (40-83)⊙ | 52 (37-74) | 52 (37-74) |
| Glucose at Detection for Meal 2, mg/dL | 157 | (149-185) | 156 (147-167) | 156 (147-167) |
| Time of Detection from Start of Meal 2, min | 45 | (30-55) | 43 (30-55) | 43 (30-55) |
| Equivalent Meal Size for Bolus, g CHO | 58 | (56-62) | 22 (15-31) | 22 (15-31) |
| Size of Meal 3, g CHO | 100 | | 100 | 100 |
| Baseline Glucose at Meal 3, mg/dL | 93 | (83-190) | 99 (84-188) | 99 (84-188) |
| Time of Meal 3 | 19:00 | | 19:00 | 19:00 |
| Peak Glucose after Meal 3, mg/dL | 279 | (222-324) | 299 (225-383) | 299 (225-383) |
| Time of Peak Glucose from Start of Meal 3, min | 87.5 | (65-115) | 103 (83-120) | 103 (83-120) |
| Time 80-180 mg/dL from Start of Meal 3 to end, % | 66 | (39-79) * | 59 (23-76) | 59 (36-76) |
| Glucose at Detection for Meal 3, mg/dL | 165 | (147-273) | 159 (154-351) | 159 (154-351) |
| Time of Detection from Start of Meal 3, min | 40 | (25-50) | 37 (25-60) | 37 (25-60) |
| Equivalent Meal Size for Bolus, g CHO | 58 | (45-79) | 24 (15-57) | 24 (15-56) |

Values are presented as median (range). Metrics that are statistically significantly different results from the unannounced (B) protocol (paired t-test, $p < 0.05$ and $p < 0.01$) are shown after the values with asterisks, *, and circled asterisks, ⊙, respectively.

What is claimed is:

1. A glucose rate increase detector (GRID) operative in conjunction with a continuous glucose monitoring (CGM) system, a controller and an insulin pump, wherein the GRID detects in a user persistent increases in glucose associated with a meal, and either triggers a meal bolus to blunt meal peak safely, during closed-loop control, or alerts the user to bolus for a meal, during open-loop control, wherein:

the GRID is configured to operate in two modes: (a) a user-input mode, in which the user enters meal information, which the GRID uses to calculate the meal bolus, and (b) an automatic mode, in which the GRID automatically calculates the meal bolus or a glucose level correction, wherein the GRID comprises an algorithm which uses CGM data to estimate the rate of change (ROC) of glucose and detect meal-related glucose excursions, the algorithm comprising:

i) a pre-processing section which uses a noise-spike filter to filter the CGM data for glucose ROC estimation, ii) an estimation section which uses the filtered CGM data to calculate glucose ROCs, and iii) a detection section which uses the calculated glucose ROCs to logically pinpoint meal events; the GRID configured to detect in the user persistent increases in blood glucose concentration associated with meal events, wherein the GRID triggers the controller to actuate the pump to deliver safe meal boluses to blunt meal peak safely, or to shift to manual control, during closed-loop control, or alerting the user to bolus for a meal, during open-loop control, wherein:

(a) the pre-processing section filters the data using a noise-spike filter:

$$G_{F,NS}(k) = \begin{cases} G_m(k) & \text{if } |G_m(k) - G_{F,NS}(k-1)| \leq \Delta G \\ G_{F,NS}(k-1) - \Delta G & \text{if } (G_{F,NS}(k-1) - G_m(k)) > \Delta G \\ G_{F,NS}(k-1) + \Delta G & \text{if } (G_m(k) - G_{F,NS}(k-1)) > \Delta G \end{cases}$$

where k is the sampling instant, $G_{F,NS}(k-1)$ is the previous filtered value from the noise spike filter, $G_{F,NS}(k)$ is the filtered value resulting from the noise-spike filter, $G_m(k)$ is the measurement, and $\Delta G$ is the maximum allowable ROC, set to 3 mg/dL in a one-minute period, to limit the ROC to a physiologically-probable value, and the data are then passed through a low pass filter to damp high frequency fluctuations:

$$G_F(k) = \frac{\Delta t}{\tau_F + \Delta t} G_{F,NS}(k) + \left(1 - \frac{\Delta t}{\tau_F + \Delta t}\right) G_F(k-1),$$

where $\Delta t$ is the sampling period, $\tau_F$ is the filter time constant, and $G_F$ is the filtered value, wherein the value for $\tau_F$ has been tuned to smooth the data without introducing a long delay to optimize the specificity and detection speed of the algorithm; or (b) in the estimation section, the ROC of glucose is calculated using the first derivative of a 3-point Lagrangian interpolation polynomial, evaluated at the most recent point, as, as follows:

$$G'_F(k) \cong \frac{t(k) - t(k-1)}{(t(k-2) - t(k-1))(t(k-2) - t(k))} G_F(k-2) +$$
$$\frac{t(k) - t(k-2)}{(t(k-1) - t(k-2))(t(k-1) - t(k))} G_F(k-1) +$$
$$\frac{2t(k) - t(k-2) - t(k-1)}{(t(k) - t(k-1))(t(k) - t(k-2))} G_F(k)$$

where k is the sampling instant, $G_{F,NS}(k-1)$ is the previous filtered value from the noise spike filter, $G_{F,NS}(k)$ is the filtered value resulting from the noise-spike filter, $G_m(k)$ is the measurement; or (c) the detection section comprises a logic wherein the detection is positive and equal to 1 at the current point only if a corresponding filtered point is above a value ($G_{min}$) and (^) either the last three ROC values are above $G'_{min,3}$ or (\/) the last two are above $G'_{min,2}$:

$$GRID^+ = \begin{cases} 1 & \text{if } G_F(k) > G_{min} \wedge ((G'_F(k-2:k) > G'_{min,3}) \vee \\ & (G'_F(k-1:k) > G'_{min,2})) \\ 0 & \text{otherwise} \end{cases}$$

wherein k is the sampling instant, $G_{F,NS}(k-1)$ is the previous filtered value from the noise spike filter, the value of $G_{min}$ is chosen large enough to isolate post-meal glucose values and to avoid the hypoglycemia region, and the ROC cutoffs are chosen to isolate post-meal rises and the hierarchical approach, with either two at a higher ROC or three at a lower ROC, allows faster detection with higher ROC values.

2. The detector of claim 1 wherein the pre-processing section filters the data using a noise-spike filter:

$$G_{F,NS}(k) = \begin{cases} G_m(k) & \text{if } |G_m(k) - G_{F,NS}(k-1)| \le \Delta G \\ G_{F,NS}(k-1) - \Delta G & \text{if } (G_{F,NS}(k-1) - G_m(k)) > \Delta G \\ G_{F,NS}(k-1) + \Delta G & \text{if } (G_m(k) - G_{F,NS}(k-1)) > \Delta G \end{cases}$$

where k is the sampling instant, $G_{F,NS}(k-1)$ is the previous filtered value from the noise spike filter, $G_{F,NS}(k)$ is the filtered value resulting from the noise-spike filter, $G_m(k)$ is the measurement, and $\Delta G$ is the maximum allowable ROC, set to 3 mg/dL in a one-minute period, to limit the ROC to a physiologically-probable value, and the data are then passed through a low pass filter to damp high frequency fluctuations:

$$G_F(k) = \frac{\Delta t}{\tau_F + \Delta t} G_{F,NS}(k) + \left(1 - \frac{\Delta t}{\tau_F + \Delta t}\right) G_F(k-1),$$

where $\Delta t$ is the sampling period, $\tau_F$ is the filter time constant, and $G_F$ is the filtered value, wherein the value for $\tau_F$ has been tuned to smooth the data without introducing a long delay to optimize the specificity and detection speed of the algorithm.

3. The detector of claim 1, wherein in the estimation section, the ROC of glucose is calculated using the first derivative of a 3-point Lagrangian interpolation polynomial, evaluated at the most recent point, as, as follows:

$$G'_F(k) \cong \frac{t(k) - t(k-1)}{(t(k-2) - t(k-1))(t(k-2) - t(k))} G_F(k-2) + $$
$$\frac{t(k) - t(k-2)}{(t(k-1) - t(k-2))(t(k-1) - t(k))} G_F(k-1) + $$
$$\frac{2t(k) - t(k-2) - t(k-1)}{(t(k) - t(k-1))(t(k) - t(k-2))} G_F(k)$$

where k is the sampling instant, $G_{F,NS}(k-1)$ is the previous filtered value from the noise spike filter, $G_{F,NS}(k)$ is the filtered value resulting from the noise-spike filter, $G_m(k)$ is the measurement.

4. The detector of claim 1, wherein the detection section comprises a logic wherein the detection is positive and equal to 1 at the current point only if a corresponding filtered point is above a value ($G_{min}$) and (^) either the last three ROC values are above $G'_{min,3}$ or (∨) the last two are above $G'_{min,2}$:

$$GRID^+ = \begin{cases} 1 & \text{if } G_F(k) > G_{min} \wedge ((G'_F(k-2:k) > G'_{min,3}) \vee (G'_F(k-1:k) > G'_{min,2})) \\ 0 & \text{otherwise} \end{cases}$$

wherein k is the sampling instant, $G_{F,NS}(k-1)$ is the previous filtered value from the noise spike filter, the value of $G_{min}$ is chosen large enough to isolate post-meal glucose values and to avoid the hypoglycemia region, and the ROC cutoffs are chosen to isolate post-meal rises and the hierarchical approach, with either two at a higher ROC or three at a lower ROC, allows faster detection with higher ROC values.

5. A health monitoring system (HMS) for real-time prediction of pending adverse events based on continuous glucose monitoring (CGM) data, comprising the glucose rate increase detector (GRID) of claim 1 and a controller, which provides prevention of the events by either a corrective action or shifting to manual control.

6. A health monitoring system (HMS) for real-time prediction of pending adverse events based on continuous glucose monitoring (CGM) data, comprising the glucose rate increase detector (GRID) of claim 2 and a controller, which provides prevention of the events by either a corrective action or shifting to manual control.

7. A health monitoring system (HMS) for real-time prediction of pending adverse events based on continuous glucose monitoring (CGM) data, comprising the glucose rate increase detector (GRID) of claim 3 and a controller, which provides prevention of the events by either a corrective action or shifting to manual control.

8. A health monitoring system (HMS) for real-time prediction of pending adverse events based on continuous glucose monitoring (CGM) data, comprising the glucose rate increase detector (GRID) of claim 4 and a controller, which provides prevention of the events by either a corrective action or shifting to manual control.

9. An artificial pancreas comprising the glucose rate increase detector (GRID) of claim 1, a low glucose predictor (LGP), a continuous glucose monitoring (CGM) device, a glucose controller, and an insulin pump, programmed and configured wherein the LGP receives CGM data from the CGM device and upon detection of low glucose, relays an alert to the user, and wherein the GRID receives CGM date from the CGM device and insulin delivery information, and upon detection of a meal, relays a bolus recommendation to the controller, which directs the pump to deliver the bolus.

10. An artificial pancreas comprising the glucose rate increase detector (GRID) of claim 2, a low glucose predictor (LGP), a continuous glucose monitoring (CGM) device, a glucose controller, and an insulin pump, programmed and configured wherein the LGP receives CGM data from the CGM device and upon detection of low glucose, relays an alert to the user, and wherein the GRID receives CGM date from the CGM device and insulin delivery information, and upon detection of a meal, relays a bolus recommendation to the controller, which directs the pump to deliver the bolus.

11. An artificial pancreas comprising the glucose rate increase detector (GRID) of claim 3, a low glucose predictor (LGP), a continuous glucose monitoring (CGM) device, a glucose controller, and an insulin pump, programmed and configured wherein the LGP receives CGM data from the CGM device and upon detection of low glucose, relays an alert to the user, and wherein the GRID receives CGM date from the CGM device and insulin delivery information, and upon detection of a meal, relays a bolus recommendation to the controller, which directs the pump to deliver the bolus.

12. An artificial pancreas comprising the glucose rate increase detector (GRID) of claim 4, a low glucose predictor (LGP), a continuous glucose monitoring (CGM) device, a glucose controller, and an insulin pump, programmed and configured wherein the LGP receives CGM data from the CGM device and upon detection of low glucose, relays an alert to the user, and wherein the GRID receives CGM date from the CGM device and insulin delivery information, and upon detection of a meal, relays a bolus recommendation to the controller, which directs the pump to deliver the bolus.

13. A method for providing a reliable layer of protection to insulin therapy, performed by the glucose rate increase detector (GRID) of claim 1 in conjunction with a continuous glucose monitoring (CGM) system, a controller and an insulin pump, the method comprising:
    operating the GRID, wherein the GRID detects in a user persistent increases in blood glucose concentration associated with meal events and either triggers a meal bolus to blunt meal peak safely, during closed-loop control, or alerts the user to bolus for a meal, during open-loop control, wherein the GRID triggers the controller to actuate the pump to deliver safe meal boluses to blunt meal peak safely, or to shift to manual control, during closed-loop control, or alerting the user to bolus for a meal, during open-loop control.

14. A method for providing a reliable layer of protection to insulin therapy, performed by the glucose rate increase detector (GRID) of claim 2 in conjunction with a continuous glucose monitoring (CGM) system, a controller and an insulin pump, the method comprising:
operating the GRID, wherein the GRID detects in a user persistent increases in blood glucose concentration associated with meal events and either triggers a meal bolus to blunt meal peak safely, during closed-loop control, or alerts the user to bolus for a meal, during open-loop control, wherein the GRID triggers the controller to actuate the pump to deliver safe meal boluses to blunt meal peak safely, or to shift to manual control, during closed-loop control, or alerting the user to bolus for a meal, during open-loop control.

15. A method for providing a reliable layer of protection to insulin therapy, performed by the glucose rate increase detector (GRID) of claim 3 in conjunction with a continuous glucose monitoring (CGM) system, a controller and an insulin pump, the method comprising:
operating the GRID, wherein the GRID detects in a user persistent increases in blood glucose concentration associated with meal events and either triggers a meal bolus to blunt meal peak safely, during closed-loop control, or alerts the user to bolus for a meal, during open-loop control, wherein the GRID triggers the controller to actuate the pump to deliver safe meal boluses to blunt meal peak safely, or to shift to manual control, during closed-loop control, or alerting the user to bolus for a meal, during open-loop control.

16. A method for providing a reliable layer of protection to insulin therapy, performed by the glucose rate increase detector (GRID) of claim 4 in conjunction with a continuous glucose monitoring (CGM) system, a controller and an insulin pump, the method comprising:
operating the GRID, wherein the GRID detects in a user persistent increases in blood glucose concentration associated with meal events and either triggers a meal bolus to blunt meal peak safely, during closed-loop control, or alerts the user to bolus for a meal, during open-loop control, wherein the GRID triggers the controller to actuate the pump to deliver safe meal boluses to blunt meal peak safely, or to shift to manual control, during closed-loop control, or alerting the user to bolus for a meal, during open-loop control.

17. The detector of claim 1:
wherein the pre-processing section filters the data using a noise-spike filter:

$$G_{F,NS}(k) = \begin{cases} G_m(k) & \text{if } |G_m(k) - G_{F,NS}(k-1)| \leq \Delta G \\ G_{F,NS}(k-1) - \Delta G & \text{if } (G_{F,NS}(k-1) - G_m(k)) > \Delta G \\ G_{F,NS}(k-1) + \Delta G & \text{if } (G_m(k) - G_{F,NS}(k-1)) > \Delta G \end{cases}$$

where k is the sampling instant, $G_{F,NS}(k-1)$ is the previous filtered value from the noise spike filter, $G_{F,NS}(k)$ is the filtered value resulting from the noise-spike filter, $G_m(k)$ is the measurement, and $\Delta G$ is the maximum allowable ROC, set to 3 mg/dL in a one-minute period, to limit the ROC to a physiologically-probable value, and the data are then passed through a low pass filter to damp high frequency fluctuations:

$$G_F(k) = \frac{\Delta t}{\tau_F + \Delta t} G_{F,NS}(k) + \left(1 - \frac{\Delta t}{\tau_F + \Delta t}\right) G_F(k-1),$$

where $\Delta t$ is the sampling period, $\tau_F$ is the filter time constant, and $G_F$ is the filtered value, wherein the value for $\tau_F$ has been tuned to smooth the data without introducing a long delay to optimize the specificity and detection speed of the algorithm; and
wherein in the estimation section, the ROC of glucose is calculated using the first derivative of a 3-point Lagrangian interpolation polynomial, evaluated at the most recent point, as, as follows:

$$G'_F(k) \cong \frac{t(k) - t(k-1)}{(t(k-2) - t(k-1))(t(k-2) - t(k))} G_F(k-2) + \frac{t(k) - t(k-2)}{(t(k-1) - t(k-2))(t(k-1) - t(k))} G_F(k-1) + \frac{2t(k) - t(k-2) - t(k-1)}{(t(k) - t(k-1))(t(k) - t(k-2))} G_F(k)$$

where k is the sampling instant, $G_{F,NS}(k-1)$ is the previous filtered value from the noise spike filter, $G_{F,NS}(k)$ is the filtered value resulting from the noise-spike filter, $G_m(k)$ is the measurement.

18. The detector of claim 1:
wherein the pre-processing section filters the data using a noise-spike filter:

$$G_{F,NS}(k) = \begin{cases} G_m(k) & \text{if } |G_m(k) - G_{F,NS}(k-1)| \leq \Delta G \\ G_{F,NS}(k-1) - \Delta G & \text{if } (G_{F,NS}(k-1) - G_m(k)) > \Delta G \\ G_{F,NS}(k-1) + \Delta G & \text{if } (G_m(k) - G_{F,NS}(k-1)) > \Delta G \end{cases}$$

where k is the sampling instant, $G_{F,NS}(k-1)$ is the previous filtered value from the noise spike filter, $G_{F,NS}(k)$ is the filtered value resulting from the noise-spike filter, $G_m(k)$ is the measurement, and $\Delta G$ is the maximum allowable ROC, set to 3 mg/dL in a one-minute period, to limit the ROC to a physiologically-probable value, and the data are then passed through a low pass filter to damp high frequency fluctuations:

$$G_F(k) = \frac{\Delta t}{\tau_F + \Delta t} G_{F,NS}(k) + \left(1 - \frac{\Delta t}{\tau_F + \Delta t}\right) G_F(k-1),$$

where $\Delta t$ is the sampling period, $\tau_F$ is the filter time constant, and $G_F$ is the filtered value, wherein the value for $\tau_F$ has been tuned to smooth the data without introducing a long delay to optimize the specificity and detection speed of the algorithm; and
wherein the detection section comprises a logic wherein the detection is positive and equal to 1 at the current point only if a corresponding filtered point is above a value ($G_{min}$) and (^) either the last three ROC values are above $G'_{min,3}$ or ($\vee$) the last two are above $G'_{min,2}$:

$$GRID^+ = \begin{cases} 1 & \text{if } G_F(k) > G_{min} \wedge ((G'_F(k-2:k) > G'_{min,3}) \vee (G'_F(k-1:k) > G'_{min,2})) \\ 0 & \text{otherwise} \end{cases}$$

wherein k is the sampling instant, $G_{F,NS}(k-1)$ is the previous filtered value from the noise spike filter, the value of $G_{min}$ is chosen large enough to isolate post-meal glucose values and to avoid the hypoglycemia region, and the ROC cutoffs are chosen to isolate post-meal rises and the hierarchical approach, with either two at a higher ROC or three at a lower ROC, allows faster detection with higher ROC values.

19. The detector of claim 1:
  wherein in the estimation section, the ROC of glucose is calculated using the first derivative of a 3-point Lagrangian interpolation polynomial, evaluated at the most recent point, as, as follows:

$$G'_F(k) \cong \frac{t(k) - t(k-1)}{(t(k-2) - t(k-1))(t(k-2) - t(k))} G_F(k-2) +$$
$$\frac{t(k) - t(k-2)}{(t(k-1) - t(k-2))(t(k-1) - t(k))} G_F(k-1) +$$
$$\frac{2t(k) - t(k-2) - t(k-1)}{(t(k) - t(k-1))(t(k) - t(k-2))} G_F(k)$$

where k is the sampling instant, $G_{F,NS}(k-1)$ is the previous filtered value from the noise spike filter, $G_{F,NS}(k)$ is the filtered value resulting from the noise-spike filter, $G_m(k)$ is the measurement; and
  wherein the detection section comprises a logic wherein the detection is positive and equal to 1 at the current point only if a corresponding filtered point is above a value ($G_{min}$) and (^) either the last three ROC values are above $G'_{min,3}$ or (\/) the last two are above $G'_{min,2}$:

$$GRID^+ = \begin{cases} 1 & \text{if } G_F(k) > G_{min} \wedge ((G'_F(k-2:k) > G'_{min,3}) \vee \\ & (G'_F(k-1:k) > G'_{min,2})) \\ 0 & \text{otherwise} \end{cases}$$

wherein k is the sampling instant, $G_{F,NS}(k-1)$ is the previous filtered value from the noise spike filter, the value of $G_{min}$ is chosen large enough to isolate post-meal glucose values and to avoid the hypoglycemia region, and the ROC cutoffs are chosen to isolate post-meal rises and the hierarchical approach, with either two at a higher ROC or three at a lower ROC, allows faster detection with higher ROC values.

20. The detector of claim 1:
  wherein the pre-processing section filters the data using a noise-spike filter:

$$G_{F,NS}(k) = \begin{cases} G_m(k) & \text{if } |G_m(k) - G_{F,NS}(k-1)| \leq \Delta G \\ G_{F,NS}(k-1) - \Delta G & \text{if } (G_{F,NS}(k-1) - G_m(k)) > \Delta G \\ G_{F,NS}(k-1) + \Delta G & \text{if } (G_m(k) - G_{F,NS}(k-1)) > \Delta G \end{cases}$$

where k is the sampling instant, $G_{F,NS}(k-1)$ is the previous filtered value from the noise spike filter, $G_{F,NS}(k)$ is the filtered value resulting from the noise-spike filter, $G_m(k)$ is the measurement, and $\Delta G$ is the maximum allowable ROC, set to 3 mg/dL in a one-minute period, to limit the ROC to a physiologically-probable value, and the data are then passed through a low pass filter to damp high frequency fluctuations:

$$G_F(k) = \frac{\Delta t}{\tau_F + \Delta t} G_{F,NS}(k) + \left(1 - \frac{\Delta t}{\tau_F + \Delta t}\right) G_F(k-1),$$

where $\Delta t$ is the sampling period, $\tau_F$ is the filter time constant, and $G_F$ is the filtered value, wherein the value for $\tau_F$ has been tuned to smooth the data without introducing a long delay to optimize the specificity and detection speed of the algorithm;
  wherein in the estimation section, the ROC of glucose is calculated using the first derivative of a 3-point Lagrangian interpolation polynomial, evaluated at the most recent point, as, as follows:

$$G'_F(k) \cong \frac{t(k) - t(k-1)}{(t(k-2) - t(k-1))(t(k-2) - t(k))} G_F(k-2) +$$
$$\frac{t(k) - t(k-2)}{(t(k-1) - t(k-2))(t(k-1) - t(k))} G_F(k-1) +$$
$$\frac{2t(k) - t(k-2) - t(k-1)}{(t(k) - t(k-1))(t(k) - t(k-2))} G_F(k)$$

where k is the sampling instant, $G_{F,NS}(k-1)$ is the previous filtered value from the noise spike filter, $G_{F,NS}(k)$ is the filtered value resulting from the noise-spike filter, $G_m(k)$ is the measurement; and
  wherein the detection section comprises a logic wherein the detection is positive and equal to 1 at the current point only if a corresponding filtered point is above a value ($G_{min}$) and (^) either the last three ROC values are above $G'_{min,3}$ or (\/) the last two are above $G'_{min,2}$:

$$GRID^+ = \begin{cases} 1 & \text{if } G_F(k) > G_{min} \wedge ((G'_F(k-2:k) > G'_{min,3}) \vee \\ & (G'_F(k-1:k) > G'_{min,2})) \\ 0 & \text{otherwise} \end{cases}$$

wherein k is the sampling instant, $G_{F,NS}(k-1)$ is the previous filtered value from the noise spike filter, the value of $G_{min}$ is chosen large enough to isolate post-meal glucose values and to avoid the hypoglycemia region, and the ROC cutoffs are chosen to isolate post-meal rises and the hierarchical approach, with either two at a higher ROC or three at a lower ROC, allows faster detection with higher ROC values.

\* \* \* \* \*